United States Patent
Hu et al.

(10) Patent No.: US 6,274,133 B1
(45) Date of Patent: *Aug. 14, 2001

(54) METHOD FOR TREATING EXTENDED-WEAR CONTACT LENSES IN THE EYES

(75) Inventors: Zhenze Hu, Pittsford; Christine E. Soltys, Rochester, both of NY (US)

(73) Assignee: Bausch & Lomb Incorporated, Rochester, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/218,869

(22) Filed: Dec. 22, 1998

(51) Int. Cl.$^7$ .............................. A61K 31/74; A67K 47/00
(52) U.S. Cl. .................... 424/78.04; 514/781; 514/912
(58) Field of Search ............................. 514/781, 912; 424/78.04

(56) References Cited

U.S. PATENT DOCUMENTS

| | | | |
|---|---|---|---|
| 4,401,327 | 8/1983 | Caines | 289/1.2 |
| 4,436,730 | * 3/1984 | Ellis et al. | 424/180 |
| 4,529,535 | * 7/1985 | Sherman | 252/106 |
| 4,748,189 | 5/1988 | Su et al. | 514/781 |
| 4,786,436 | 11/1988 | Ogunbiyi et al. | 252/352 |
| 5,209,865 | 5/1993 | Winterton et al. | 252/174 |

FOREIGN PATENT DOCUMENTS

| | | | |
|---|---|---|---|
| 93 05085 A | 3/1993 | (WO) | C08F/299/08 |
| 95 00620 A | 1/1995 | (WO) | C11D/3/00 |

OTHER PUBLICATIONS

Poggio, Eugene C., "Complications and Symptoms in Disposable Extended Wear Lenses Compared with Conventional Soft Daily Wear and Soft Extended Wear Lenses" *CLAO Journal*, vol. 19, No. 1 (Jan. 1993).

Franklin, V., et al. "Early Deposition Trends on Group I (Polymacon and Tetrafilcon A) and Group III (Bufilcon A) Materials" *CLAO Journal*, vol. 17, No. 4 (Oct. 1991).

Binder, P.S., "Complications Associated With Extended Wear in Daily Soft Contact Lens" *Ophthalmology*, vol. 86, No. 6 (Jun. 1979).

Hart, Dean E., "Lipid Deposits Which Form on Extended Wear Contact Lenses", *International Contact Lens Clinic*, vol. 11, No. 6 (Jun. 1984).

Hart, Dean E., et al., "Origin and Composition of Lipid Deposits on Soft Contact Lenses" *Ophthalmology*, vol. 93, No. 4 (Apr. 1986).

Caroline, Patrick J., "Microscopic and Elemental Analysis of Deposits on Extended Wear Soft Contact Lenses" *CLAO Journal*, vol. 11,, No. 4 (Oct. 1985).

Hathaway, Rodney A., et al., "Soft Lens Cleaners: Their Effectiveness in Removing Deposits" *Journal of the American Optometric Association*, vol., No. 3 (Mar. 1978).

Joanny, J.F., "Polyelectrolyte Adsorption and Charge Inversion" *Eur. Phys. J.*, vol. 9, No. 1 (1999).

Donath, E., "Nonlinear Hair Layer Theory of Electrophoretic Fingerprinting Applied to Consecutive layer By Layer Polyelectrolyte" *Langmuir*, vol. 13, No. 20 (1997).

Pedrotti, M., Guerra, G. F., "Advantages of Hard Gas–Permeable Lenses with High Dk in Extended Wear" *Boll Ocul*, vol. 67, No. 1 (1988) (English language abstract of article published in Italian).

* cited by examiner

*Primary Examiner*—Zohreh Fay
(74) *Attorney, Agent, or Firm*—Robert B. Furr, Jr.

(57) ABSTRACT

The present invention is directed to a method for treating a silicone-hydrogel contact lenses while worn in the eye. In particular, the method employs an ophthalmic solution containing a cationic cellulosic polymer that binds to the lens and prevents the accumulation of lipids, proteins and other products, particularly during extended use of the lens. The addition of one or more surfactants to the solution further maintains the lens clean during use. Such a solution is intended to be applied, in the form of drops, to contact lens in the eye.

13 Claims, No Drawings

METHOD FOR TREATING EXTENDED-WEAR CONTACT LENSES IN THE EYES

FIELD OF THE INVENTION

This invention relates to a method for treating extended-wear contact lenses while they are worn in the eyes. In particular, the present invention is directed to a method of applying solution that can be applied in the form of eyedrops to a contact lens while it is worn in the eye. The method is especially useful for preventing the deposition of lipid and lipid-like substances on extended-wear silicone-hydrogel contact lenses.

BACKGROUND OF THE INVENTION

Contact lenses in wide use today fall into two categories. First, there are the hard or rigid corneal type lenses that are formed from materials prepared by the polymerization of acrylic esters, such as polymethylmethacrylate (PMMA). Secondly, there are the gel, hydrogel or soft type of lenses made by polymerizing such monomers as 2-hydroxyethyl methacrylate (HEMA). Finally, there is a new class of high Dk soft lenses made from polymers comprising silicone-containing monomers and/or macromonomers.

Contact lenses made from silicone-containing materials have been investigated for a number of years. Such materials can generally be subdivided into two major classes, namely hydrogels and non-hydrogels. Non-hydrogels do not absorb appreciable amounts of water, whereas hydrogels can absorb and retain water in an equilibrium state. Regardless of their water content, both non-hydrogel and hydrogel silicone contact lenses tend to have relatively hydrophobic, non-wettable surfaces.

Those skilled in the art have long recognized the need for modifying the surface of such silicone contact lenses so that they are compatible with the eye. It is known that increased hydrophilicity of the contact lens surface improves the wettability of the contact lenses. This in turn is associated with improved wear comfort of contact lenses. Additionally, the surface of the lens can affect the lens's susceptibility to deposition, particularly protein and lipid deposition from the tear fluid during lens wear. Accumulated deposition can cause eye discomfort or even inflammation. In the case of extended-wear lenses, the surface is especially important since extended wear lens must be designed for high standards of comfort over an extended period of time, without requiring daily removal of the lens before sleep. Thus, the regimen for the use of extended-wear lenses would not provide a period of time on a daily basis for the eye to rest or recover from any discomfort or other possible adverse effects due to lens wear during the day.

The patent literature has disclosed various surface treatments for rendering the surface of silicone lenses more hydrophilic and more wettable, including changing the chemistry of the surface layer, coating the surface, and compounding the polymer with additives that subsequently diffuse to the surface. Among chemical surface modification techniques are non-polymeric plasma treatments and corona treatments. The surface of a contact lens can also be modified, at least temporarily and to various degrees, by treatment with contact-lens care solutions.

Solutions that wet the lenses before insertion in the eye are required for both the hard and soft types of contact lenses, at least for non-disposable lens or lenses that are reused at least once after being worn. Surfactant cleaning agents in daily lens care solutions are useful for the removal of lens lipids. Also, the use of enzymes or equivalent protein removing agents has been conventional. With the advent of extended wear lenses, however, in which lenses are worn overnight and even continuously over a plurality of days, the conventional lens care solutions no longer have the opportunity to remove depositions that have accumulated over the day with daily cleaning solutions. Also, because of the hyrdrophobicity of silicone hydrogel materials, they are especially susceptible to the deposition of lipid or lipid-like materials.

It would therefore be desirable to have a solution that could be applied to the eye in order to accomplish cleaning and/or prevent the deposition of lipids or other materials until such time as the lens is removed from the eye and cleaned or disposed.

It does not necessarily follow that cleaning agents that can used in cleaning solutions in which the contact lenses are immersed for several hours or more would be effective when applied in the form of eyedrops. In particular, cleaning agents that are designed to prevent the deposition of lipids on the lens must have an extended effect in conjunction with the lens. At the same time, cleaning agents must be selected that are very safe and comfortable, especially as they would be expected to associate with the lens surfaces. Eye irritation must be avoided.

Ophthalmic solutions for rewetting, lubricating, and/or enhancing wearer comfort by application to the eye or a contact lens while being worn in the eye, are known. Rewetting solutions usually contain a wetting agent in combination with a germicide or preservative, a viscosity builder, and salts that adjust the tonicity of the solutions to make them compatible with the osmolality of tear fluids. Isotonic solutions for improving the comfort of wearing soft contact lenses are known. Such solutions typically may also contain lubricants or demulcents, surfactants, and.or buffers.

For example, U.S. Pat. No. 4,529,535 to Sherman discloses a rewetting solution that is particularly useful for silicone contact lenses, including extended wear lenses. One embodiment includes the combination of hydroxyethylcellulose, polyvinyl alcohol, and polyvinylpyrrolidone. U.S. Pat. No. 4,786,436 to Ogunbiyi discloses a wetting solution comprising collagen and other demulcents such as hydroxylethyl cellulose, methyl cellulose, carboxymethyl cellulose, hydroxypropyl methyl cellulose, hydroxylpropylcellulose and the like.

U.S. Pat. No. 4,748,189 to Su et al. discloses an ophthalmic solution for improving the exchange of fluid in the area outside a hydrogel contact lens in the area underneath the hydrogel contact lens, in order to permit tear exchange to occur, thereby preventing the accumulation of waste matter and debris under the lens. The solution contains a hydrogel flattening agent, for example urea, glycerin, propylene glycol, sorbitol or an amino ethanol. Surfactants that are useful in the solution include poloxamer and tyloxapol. Suitable lubricants include hydroxylethyl cellulose, polyvinylalchol, and polyvinylpyrrolidone.

U.S. Pat. No. 5,209,865 to Winterton et al. discloses a conditioning solution for contact lenses that comprises a combination of a poloxamine and a poloxamer surfactant each having an HLB (hydrophilic-lipophilic balance) of seven or below. The solution according to the invention forms a uniform hydrophilic film on a lens surface for which proteins have very little affinity. As such, a contact lens contacted by the solution is said to have a coating that provides a prophylactic effect to the lens.

U.S. Pat. Nos. 4,436,730 and 4,401,327 to Ellis et al. disclose the use of cationic cellulosic derivatives in contact-lens treating solutions, including the combination of a cationic cellulose such as polymer JR-30M and an ethoxylated glucose such as glucam. In column 4, lines 42–57, Ellis et al. state that the combination of a cationic cellulose material with a PEO (polyethyleneoxide) component such as glucam is particularly advantageous for the reason that the cationic component complexes with the PEO component and the complex more strongly adsorbs on the lens surface. The cationic cellulose polymer and entangled PEO are believed to reach into the aqueous phase to provide cushioning and protein resistance. The invention covered by these patents, however, have been used in products for RGP (rigid-gaspermeable) silicone-containing lenses as compared to soft lenses. There is no mention of such solutions preventing the deposition of lipids on extended-wear lenses made from silicone hydrogels.

In view of the above, it would be desirable to provide an eye-drop solution that can be safely and efficaciously used for both lubricating and/or rewetting contact-lens in the eye and, at the same time, serve to prevent the accumulation of lipids or the like on the contact lens while it is worn in the eye.

SUMMARY OF THE INVENTION

The present invention is directed to a method of rewetting silicone hydrogel contact lens while also providing resistance to protein and lipid deposition. The solution employed in the invention comprises a cationic cellulose derivative. Such an solution is applied in the form of drops to the contact lens while they are in the eye. The method also employs an eye-drop dispenser (eyedropper) and a plastic container holding between about 1 and about 30 ml of an ophthalmic solution that comprising an effective amount of cationic cellulosic derivative. In one embodiment of the invention, the solution also comprises an effective amount of a polymeric demulcent. Preferably, the polymeric demulcent is a polyvinylpyrollidone polymer. Such a solution is especially advantageous for the treatment of soft lenses that are capable of use for extended wear, particularly silicone hydrogel lenses that potentially can be worn for about seven days and even longer. Additional ingredients that maybe included in the solution employed in the present invention include a sequestering agent which is present in an amount of 0.01 to 2.0% by weight and an effective amount of a buffering agent. The objects, features, and advantages of the various embodiments of the present invention will become more readily apparent from the following detailed description.

DETAILED DESCRIPTION OF THE INVENTION

The present invention is directed to a method rewetting or lubricating a contact lens while it is worn in the eye and which is also useful for prophylactically cleaning the lens by preventing the deposition of lipids or other depositions on the lens. In particular, the present invention is useful with respect to extended-wear lenses that are made from a silicone-hydrogel material. Lenses made from silicone-hydrogel materials are more hydrophobic that other types of soft lenses and are, therefore, especially prone to lipid deposition which may present a problem during the extended use of such lenses. Hydrogels in general are a well known class of materials which comprise hydrated, cross-linked polymeric systems containing water in an equilibrium state. Silicone hydrogels generally have a water content greater than about 5 weight percent and more commonly between about 10 to about 80 weight percent. Such materials are usually prepared by polymerizing a mixture containing at least one silicone-containing monomer (including macromonomers) and at least one hydrophilic monomer. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Another class of representative silicon-containing monomers includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy) silane]; 3-[tris(tri-methylsiloxy)silyl] propyl vinyl carbamate; 3-[tris(trimethylsiloxy)silyl] propyl allyl carbamate; 3-[tris(trimethylsiloxy)silyl]propyl vinyl carbonate; t-butyldimethyl-siloxyethyl vinyl carbonate; trimethylsilylethyl vinyl carbonate; and trimethylsilylmethyl vinyl carbonate.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacrylates in Polyurethane-Polysiloxane Hydrogels," *Journal of Applied Polymer Science*, Vol. 60, 1193–1199 (1996). PCT Published Application No. WO 96/31792 discloses examples of such monomers, which disclosure is hereby incorporated by reference it its entirety.

A preferred silicone hydrogel material comprises (in bulk formula, that is, in the monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer, as a percentage of the hydrogel polymer material. In general, the silicone macromonomer is a poly(organosiloxane) capped with an unsaturated group at one or more ends of the molecule, typically two or more ends for copolymerization. In addition to the end groups in the above mentioned-patents, U.S. Pat. No. 4,153,641 to Deichert et al. discloses additional unsaturated groups, including acryloxy or methacryloxy.

Suitable hydrophilic monomers for use in silicone hydrogels include, for example, unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone (NVP); and acrylamides, such as methacrylamide and N,N-dimethylacrylamide, and the like. Still further examples are the hydrophilic vinyl carbonate or vinyl carbamate monomers disclosed in U.S. Pat. Nos. 5,070,215, and the hydrophilic oxazolone monomers disclosed in U.S. Pat. No. 4,910,277.

The lens-care ophthalmic solution of the present invention have been found to be particularly effective for use with silicone-hydrogel contact lenses as described above, which may be coated with materials or surface-modified to mask to some extent the hydrophobic nature of the core material. (See, for example, commonly assigned U.S. Ser. No. 60/084,334, hereby incorporated by reference in its entirety.)

Solutions according to the present invention typically involve the combination of about 0.01 to 1.0 percent by weight of a cationic cellulosic polymer and at least one tonicity agent which is present in an amount of 0.01 to 10.0% by weight, an effective amount of a buffering agent. In one embodiment, the solution also comprises a polymeric demulcent. It has been found that this particular combination of ingredients is both comfortable for use in the eye and effective in preventing the deposition of lipids. Without wishing to be bound by theory, the cationic cellulosic polymer is believed to complex with the lens surface. The cationic cellulosic polymer may further anchor other components such as any optional surfactant and.or polymeric demulcent on the surface and the entangled surfactant or demulcent may reach into the aqueous phase to provide further cushioning and deposit resistance. These separate functions, however, should not be viewed as clearcut and exclusive. Any surfactants may also loosen deposits on the lens; wherein removal is assisted by the natural cleaning action of blinking. The cellulosic polymer, by providing ionic charge, in particular, may inhibit the deposition of lipids because it renders the surface less hydrophobic.

Any suitable cationic cellulosic material may be used in the practice of this invention. Examples include cellulosic polymers containing N,N-dimethyl amino ethyl groups (either protonated or quaternized) and cellulosic polymers containing N, N-dimethyl amino-2-hydroxylpropoyl groups (either protonated or quatemized). Cationic cellulosic polymers are commercially available or can be prepared by methods known in the art. As an example, the quaternary nitrogen-containing ethoxylated glucosides can be prepared by reacting hydroxyethyl cellulose with a trimethyl ammonium substituted epoxide. Various preferred cationic cellulosic polymers are commercially available water soluble polymers available under the CTFA (Cosmetic, Toiletry, and Fragrance Association) designation Polyquaternium-10, including the cationic cellulosic polymers available under the tradename UCARE® Polymer from Amerchol Corp., Edison, N.J., USA). These polymers contain quatemized N,N-dimethyl amino groups along the cellulosic polymer chain.

The cationic cellulosic component may be employed in the compositions at about 0.001 to about 10 weight percent of the composition, preferably at about 0.02 to about 5 weight percent, with about 0.05 to about 2 weight percent being especially preferred. Suitable cationic cellulosic material have the following formula:

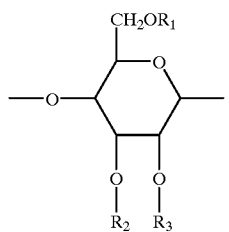

Where $R_1$, $R_2$ and $R_3$ are selected from H, derivatives of $C_1$–$C_{20}$ carboxylic acid, $C_1$–$C_{20}$ alkyl groups, $C_1$ to $C_3$ monohydric and dihydric alkanols, hydroxyethyl groups, hydroxypropyl groups, ethylene oxide groups, propylene oxide groups, phenyl groups, "Z" groups and combinations thereof.

The nature of the "Z" groups are:

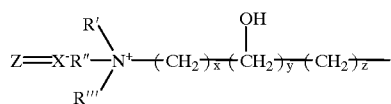

where:

R', R" and R'" can be H, $CH_3$, $C_2H_5$, $CH_2CH_2OH$ and

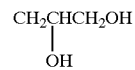

x=0–5, y=0–4, and z=0–5

$X^- = Cl^-$, $Br^-$, $I^-$, $HSO_4^-$, $CH_3SO_4^-$, $H_2PO_4^-$, or $NO_3^-$

The solutions employed in the present invention preferably also contains a polyoxyethylene-polyoxypropylene nonionic surfactant which, for example, can be selected from the group of commercially available surfactants having the name poloxamine or poloxamer, as adopted by The CTFA International Cosmetic Ingredient Dictionary. The poloxamine surfactants consist of a poly(oxypropylene)-poly(oxyethylene) adduct of ethylene diamine having a molecular weight from about 7,500 to about 27,000 wherein at least 40 weight percent of said adduct is poly (oxyethylene), has been found to be particularly advantageous for use in conditioning contact lenses when used in amounts from about 0.01 to about 15 weight percent. Such surfactants are available from BASF Wyandotte Corp., Wyandotte, Mich., under the registered trademark "Tetronic". The poloxamers are an analogous series of surfactants and are polyoxyethylene, polyoxypropylene block polymers available from BASF Wyandotte Corp., Parsippany, N.J. 07054 under the trademark "Pluronic".

The HLB of a surfactant is known to be a factor in determining the emulsification characteristics of a nonionic surfactant. In general, surfactants with lower HLB values are more lipophilic, while surfactants with higher HLB values are more hydrophilic. The HLB values of various poloxamines and poloxamers are provided by BASF Wyandotte Corp., Wyandotte, Mich. Preferably, the HLB of the surfactant in the present invention is at least 18, more preferably 18 to 32, based on values reported by BASF.

Additional compatible surfactants that are known to be useful in contact wetting or rewetting solutions can be used in the solutions of this invention. The surfactant should be soluble in the lens care solution and non-irritating to eye tissues. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available from ICI Americas Inc., Wilmington, Del. 19897 under the trademark Tween® 20), polyoxyethylene (23) lauryl ether (Brij® 35), polyoxyethylene (40) stearate (Myrj® 52), polyoxyethylene (25) propylene glycol stearate (Atlas® G 2612). Brij® 35, Myrj® 52 and Atlas® G 2612 are trademarks of, and are commercially available from, ICI Americas Inc., Wilmington, Del. 19897.

Various other surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C.

As indicated above, a polymeric demulcent can be advantageously included in the solution employed in the present invention. The demulcent provides wetting, moisturizing, and/or lubricating of contact lens in the eyes of wearers, resulting in their increased comfort. The polymeric demulcent can also act as a water-soluble viscosity builder. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose, povidone, polyvinyl alcohol, and the like. Such viscosity builders or demulcents may be employed in a total amount ranging from about 0.01 to about 5.0 weight percent or less. Suitably, the viscosity of the final formulation is 10 cps to 50 cps. Comfort or wetting agents such as glycerin or propylene glycol can also be added and the latter is particularly preferred, for example, in amounts ranging from 0.01 to 2.0 percent by weight of the solution. Other suitable wetting agents include mono or disaccharide, polyethylene glycol, ethoxylated glucose, and the like.

A preferred demulcent is povidone (polyvinylpyrrolidone or PVP), which is a Category I demulcent in the OTC Ophthalnic Drug Products Monograph of the USFDA. Polyvinylpyrrolidone (PVP) is a linear homopolymer or copolymer comprising at least about 80%, preferably at least about 90% of repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrrolidinone, and 1-ethenyl-2-pyrolionone (CAS registry number 9003–39–8). PVP has a weight average molecular weight of about 10,000 to 250,000, preferably 30,000 to 100,000. Such materials are sold by various companies, including ISP Technologies, Inc. under the trademark PLASDONE™ K-29/32, BASF under the trademark KOLLIDON™ for USP grade PVP, for example KOLLIDON™ K-30 or K-90 (BASF Corporation, NV Division, 3000 Continental, Mount Olive, N.J. 07628–1234, USA). In the present compositions, the PVP is suitably present in an amount 0.01 to 10.0% by weight, preferably of between 0.05 to 5.0 percent by weight.

The present composition will contain a disinfecting amount of a preservative or an antimicrobial agent. A particularly preferred preservative is sorbic acid (0.15%). Antimicrobial agents are defined as organic chemicals which derive their antimicrobial activity through a chemical or physiochemical interaction with the microbial organisms. For example, biguanides include the free bases or salts of alexidine, chlorhexidine, hexamethylene biguanides and their polymers, and combinations of the foregoing. The salts of alexidine and chlorhexidine can be either organic or inorganic and are typically gluconates, nitrates, acetates, phosphates, sulphates, halides and the like. Other preferred antimicrobial agents are the polymeric quaternary ammonium salts used in ophthalmic applications and the biguanides, for example, the hexamethylene biguanides (commercially available from Zeneca, Wilmington, DE under the trademark Cosmocil™ CQ), their polymers and water-soluble salts. Generally, the hexamethylene biguanide polymers, also referred to as polyaminopropyl biguanide (PAPB), have molecular weights of up to about 100,000. Such compounds are known and are disclosed in U.S. Pat. No. 4,758,595 and British Patent 1,432,345, which patents are hereby incorporated herein by reference. The hydrochloride salt of polyhexamethylene biguanide is commercially available from Zeneca, Inc. under the trademark Cosmocil® CQ. This biguanide is often referred to as either "PHMB" or "PAPB," as herein, usually by the latter acronym corresponding to polyaminopropyl biguanide.

In addition to the active ingredients described above, solutions employed in the present invention may contain buffers, stabilizers, isotonic agents and the like which aid in making ophthalmic compositions more comfortable to the user. The aqueous solutions of the present invention are typically adjusted with tonicity agents to approximate the osmotic pressure of normal lachrymal fluids which is equivalent to a 0.9% solution of sodium chloride or 2.5% of glycerol solution. The solutions are made substantially isotonic with physiological saline used alone or in combination, otherwise if simply blended with sterile water and made hypotonic or made hypertonic the lenses will lose their desirable optical parameters. Correspondingly, excess salt or other tonicity agent may result in the formation of a hypertonic solution which will cause stinging and eye irritation. An osmolality of about 225 to 400 mOsm/kg is preferred, more preferably 280 to 320 mOsm/kg.

The pH of the present solutions should be maintained within the range of 5.0 to 8.0, more preferably about 6.0 to 8.0, most preferably about 6.5 to 7.8. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred, particularly for enhancing the efficacy of PAPB. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

As indicated above, the present invention is usefull for cleaning a contact lens while it is worn in the eye. Thus, as mentioned above, compositions of the present invention are especially advantageous with people who are prone to heavy lipid or other deposition or who where lenses under an extended wear regime. Extended wear is defined as a lens that is worn overnight, during sleep, preferably capable of wear for a week, more preferably for two weeks, and most preferably for about one month.

The compositions of the present invention can be provided in a wide range of small volume containers, typically 1 to 30 ml in size, preferably 1 ml to 20 ml in size. Such containers can be made from HDPE (high density polyethylene), LDPE (low density polyethylene), polypropylene, poly(ethylene terepthalate) and the like. Flexible bottles having conventional eye-drop dispensing tops are especially suitable for use with the present invention.

Compositions employed in the present invention can be applied as follows. During wear, about two or three drops may be placed directly onto each lens whenever needed. Thereafter, the wearer should blink several times. After waiting a few moments, if the lens still does not feel comfortable, another drop or two can be added.

The following specific experiments and examples demonstrate the method of the present invention and a solution employed in the method. However, it is to be understood that these examples are for illustrative purposes only and do not purport to be wholly definitive as to conditions and scope. All percentages are by weight of the solution, unless indicated otherwise. The examples presented are provided as a further guide to the practitioner of ordinary skill in the art and are not to be construed as limiting the invention in any way.

EXAMPLE 1

This example discloses the preparation of a representative silicone hydrogel lens material used in the following Examples. The formulation for the material is provided in Table 1 below.

TABLE 1

| Component | Parts by Weight |
|---|---|
| TRIS-VC | 55 |
| NVP | 30 |
| $V_2D_{25}$ | 15 |
| VINAL | 1 |
| n-nonanol | 15 |
| Darocur | 0.2 |
| tint agent | 0.05 |

The following materials are designated above:

TRIS-VC tris(trimethylsiloxy)silylpropyl vinyl carbamate

NVP N-vinyl pyirolidone $V_2D_{25}$ a silicone-containing vinyl carbonate as previously described in U.S. Pat. No. 5,534,604.

VINAL N-vinyloxycarbonyl alanine

Darocur Darocur-1173, a UV initiator tint agent 1,4-bis[4-(2-methacryloxyethyl) phenylamino] anthraquinone Silicone-hydrogel lenses made of the above formulation were cast molded from polypropylene molds. Under an inert nitrogen atmosphere, 45-μl of the formulation was injected onto a clean polypropylene concave mold half and covered with the complementary polypropylene convex mold half. The mold halves were compressed at a pressure of 70 psi and the mixture was cured for about 15 minutes in the presence of UV light (6–11 mW/cm$^2$ as measured by a Spectronic UV meter). The mold was exposed to UV light for about 5 additional minutes.

The top mold half was removed and the lenses were maintained at 60° C. for 3 hours in a forced air oven to remove n-hexanol. Subsequently, the lens edges were ball buffed for 10 seconds at 2300 rpm with a force of 60 g. The lenses were then plasma treated as follows: The lenses were placed concave side up on an aluminum coated tray and the tray placed into a plasma treatment chamber. The atmosphere was produced by passing air at 400sccm into the chamber through an 8% peroxide solution, resulting in an Air/$H_2O$/$H_2O_2$ gas mixture. The lenses were plasma treated for a period of 8 minutes (350 watts, 0.5 torr). The chamber was then backfilled to ambient pressure. The tray was then removed from the chamber, the lenses flipped over, and the procedure repeated to plasma treat the other side of the lenses. The plasma chamber was a direct current DC RFGD chamber manufactured by Branson GaSonics Division (Model 7104). This chamber was a cold equilibrium planar configuration which had a maximum power of 500 watts. Prior to any plasma treatnent, the lenses in the chamber were prepumped to 0.01 torr to remove residual air in the chamber. Following plasma treatment, fall processing included extraction, hydration and autoclave sterilization. Extraction employed isopropanol at room temperature for 4 hours (during commercial manufacture a minimum of 48 hours following by extraction in water at about 85° C. for 4 hours is preferred). The lenses were then immersed in buffered saline for hydration. Autoclaving was carried out with the lenses, within vials, immersed in an aqueous packaging solution.

EXAMPLE 2

An aqueous solution employed in the invention, useful for treating sillicone hydrogel contact lenses worn in the eye, is prepared with the following ingredients in water:

TABLE 2

| Ingredient | Mg/g | % w/w |
|---|---|---|
| Polymer JR | 70.0 | 0.070 |
| Tetronic 1107 | 500.0 | 0.500 |
| PVP K30 | 200.0 | 0.200 |
| Sorbic Acid | 165.0 | 0.165 |
| Boric Acid | 677.0 | 0.677 |
| Sodium Borate | 236.0 | 0.236 |
| Sodium Phosphate (Dibasic) | 310.0 | 0.310 |
| Sodium Chloride | 43.0 | 0.043 |
| Potassium Chloride | 83.0 | 0.083 |
| Propylene Glycol | 300.0 | 0.300 |
| Edetate Disodium | 50.0 | 0.050 |
| Distilled Water | Q.S. 1 g | Q.S. to 100% |

The formulation is prepared in bulk as follows. In a 316-grade stainless steel jacketed pressure kettle equipped with agitation, distilled water is added in the amount of about 50–55% of the total batch weight. The water is heated to 75 to 85° C. and with continuted agitation the following batch quantities of the following ingredients are added, wherein after one ingredient is dissolved or hydrated, the next is added: sodium chloride, potassium chloride, boric acid, sodium borate,disodium edetate, PVP K-30, and Polymer JR 30M. The batch is heat sterilized at 121.1 to 123° C. for a minimum of 30 minutes. The total heat sterilization time has a desired target of 30–35 minutes, not to exceed 40 minutes. With continuted agitation, the batch is cooled down with recirculating cold water through the outside jacket to a temperature not greater than 40C while maintaining positive internal pressure with sterile air. In a second phase of preparation, purified water is added to an appropriate clean mixing vessel to 35 to 40% of the total batch weight. With continued agitation, the following ingredients are added in the order listed: sodium phosphate, sorbic acid, the poloxamine, and propylene glycol, allowing each to dissolve or disperse before adding the next. This second solution is transferred to the first solution through a prefilter and sterilizing filter. The second-phase vessel and the filters are rinsed with a volume of purified water equivalent to 5 to 10% of the total batch weight. The batch is subjected to continued mixing while cooling the product to 20–35° C. for a minimum of 30 minutes. If necessary, the pH is adjusted to 7.0–7.40 at 25° C. with 2.5 N NaOH or 1N HCl. The finished solution should be aseptically passed through a sterile polishing filter prior to bottling.

EXAMPLE 3

This example illustrates the advantageous properties of a solution according to the present invention. In particular, contact lenses as described in Example 1 (hereafter "balafilcon A contact lenses") were deposited using both a protein and lipid artificial deposition solution (ATS) respectively in order to assess the deposit inhibition of the formulation according to Example 1 ("Formulation A") compared to ReNu® Rewetting Drops as the control test solution ("Comparative Formulation B").

To test for deposit inhibition, lenses were pre-conditioned with the Formulation A by soaking the lens in the solution for one hour prior to deposition. Seven lenses were deposited for the Formulation A as well as for the Control lenses (to determine baseline protein and lipid levels). After deposition and incubation, the lenses were then rinsed with ReNu® Saline (no sorbic acid) and analyzed for protein and lipid levels respectively. The testing was conducted as follows:

A. Protocol for testing Protein Deposit Inhibition

In the preparation of the standards, unworn balafilcon A lenses are taken out of their vials, left to air dry and then placed in glass test tubes along with standard BSA solution. An in vitro protein mixture consisting of lysozyme, lactoferrin, human serum albumin and mucin in MOPS buffer was used. The pH of the solution is adjusted to 7.2 using 1N HCl and an osmolality equal to 326 mOsm. Seven balafilcon A lenses per test solution were preconditioned with the respective test formulations by soaking the lens in the formulation for one hour. The lenses were then removed from the formulation, and placed in 1.5 mls of the Protein Mix. The lenses were then incubated in the Protein Mix at 37° C. in a shaking water bath for 48 hours. Protein analysis was done using the colorimetric BCA analytical method (Sigma). The method employs the protein induced reduction of Cu(II) to Cu(I). A purple complex (Amax=562 nm) is formed following the addition of Bicinchoninic acid (BCA) to the reduced copper. The intensity of the complex is shown to be directly proportional over the protein concentration range 5 $\mu$g/ml to 2000 $\mu$g/ml. Following incubation at 37° C., the rate of color development is slowed sufficiently to allow large numbers of samples to be done in a single run. The standard protein solution utilized was BSA with a standard concentration range of 0–50 $\mu$g. To each test tube was added 2 mls of a mixture of Bicinchoninic acid (BCA) and Cu(II) Sulfate and vortexed. Tubes were then covered and placed in a water bath at 37° C. for 15 minutes. After incubation, the purple complex develops. Samples and standards are read at 562 nm in a Perkin Elmer Spectrophotometer. Protein concentration is determined from a Standard plot of Absorbency vs. Concentration ($\mu$g). Protein results reported represent total amount of bound protein.

B. Protocol for testing Lipid Deposit Inhibition:

Seven balafilcon A lenses per test solution were preconditioned with the respective test formulations by soaking the lens in the formulation for one hour. The lenses were then removed from the formulation, and placed in 1.5 mls of a Lipid Mix. The Lipid Mix was a mixture of palmitic acid methyl ester (PAME), cholesterol, squalene and mucin in MOPS buffer. Mucin is utilized as a surfactant to aid in the solubilization of the lipids. Lenses were then incubated in the Lipid Mix at 37° in a shaking water bath for 24 hours. After incubation, the lenses were then removed from the test solution and rinsed with ReNu® Saline (no sorbic acid) to remove any residual deposition solution. Lenses were then placed in glass vials for extraction. A three hour 1:1 CHCl$_3$/MeOH extraction was subsequently followed by a three hour hexane extraction. Extracts were then combined and run on a Hewlett Packard Gas Chromatograp (GC) utilizing an HP Ultra I column with an FID detector and He as the carrier gas. Standard solutions of each of the lipids in the deposition mix were made in 1:1 CHCl$_3$/MeOH and the concentration of lipid extracted from the lenses was determined.

C. The Results:

The % Deposit Inhibition for protein and lipid, respectively, was calculated by the following equation:

% Deposit Inhibition=(Avg. of Control deposited lens-Avg. of Treated lens)*100 Avg. of Control deposited lens where the control lens is a balafilcon A lens deposited with the protein and lipid solution respectively.

The protein and lipid deposition values for the balafilcon A control lenses (7.75 $\mu$g and 381 $\mu$g), respectively, provided a baseline with which to assess the potential cleaning efficacy and deposit inhibition attributes of each of the formulations tested. Table 3 below represents the protein raw data and deposit inhibition results relative to the control deposited lenses. Table 4 below represents the lipid raw data and deposit inhibition results relative to the control deposited lens.

TABLE 3

Protein Deposit Inhibition and Cleaning Efficacy Data

| Test Formulation | Average Protein Deposition on Balafilcon A Control lenses | Average Protein Levels for Deposit Inhibition ($\mu$g) | % Total Protein Deposit Inhibition |
| --- | --- | --- | --- |
| Formulation A | 7.75 ug | 6.46 ug | 16.6 |
| Comparative Form. B | 7.75 ug | 6.46 ug | 16.6 |

TABLE 4

Lipid Deposit Inhibition and Cleaning Efficacy Data and Results

| Test Formulation | Average Lipid Deposition on Balafilcon A Control lenses | Average Lipid Levels for Deposit Inhibition ($\mu$g) | % Total Lipid Deposit Inhibition |
| --- | --- | --- | --- |
| Formulation A | 381 $\mu$g | 195 $\mu$g | 34.5 |
| Comparative Form. B | 381 $\mu$g | 321 $\mu$g | 15.7 |

With respect to protein deposit inhibition, the data for the test formulation were relatively close in comparison to the control deposited lens. As shown in Table 4, however, the Formulation A appears to inhibit lipid deposition indicating that the test formulations are coating the lens in such a way as to hinder lipid uptake. Since lipid deposition is the main concern with respect to the silicone hydrogel lenses, the Formulation A would be highly effective in preventing unwanted depositions.

EXAMPLE 4

The objective of this study was to evaluate the safety and tolerability of a continuous wear rewetting drop compared to the currently marketed ReNu® Rewetting Drops while wearing balafilcon A tinted contact lenses for 4 hours. Twenty (20) subjects were enrolled in a 4 hour non-dispensing study comparing Formulation A (Example 2) to ReNu® Rewetting Drops. All subjects were habitual soft spherical contact lens wearers, with Mean spherical Rx's of−3.25D in the test eyes, and −3.00D in the control eyes. Subjects in both groups had less than 0.75D refractive cylinder. Each subject wore a pair of balafilcon A tinted contact lenses for approximately 4 hours. The eye receiving the test solution was randomly selected and remained constant for the duration of the study. Subjects were asked to place two drops of each solution into the appropriate eyes every hour until the four hour visit. The subjects and investigator were masked to solution identity. Prior to lens insertion a spherical refraction was performed through which high contrast visual acuity with high ambient illumination (HCHI) was measured. Corneal and conjunctival staining and limbal and bulbar injection were assessed with the slitlamp. Each subject was then fitted with a pair of balafilcon A tinted lenses of their power. Each lens was evaluated for centration and movement, comfort, and deposits/wettability. A spherical over refraction was then performed. The endpoint of the over refraction was compared to the refractive endpoint to determine the apparent "on-eye" lens power. LogMAR visual acuity under HCHI testing conditions was measured through the over-refraction. Finally, two drops of each solution were instilled into the appropriate eyes and the subject was asked to rate any sting/burn and the amount. Testing was repeated at the four hour visit in reverse order, with the exception that the baseline refraction was not repeated.

Unless otherwise noted, a 2-way ANOVA incorporating Time and Solution was used to test for differences in each of the parametric dependent variables measured. Non-parametric data was analyzed by Friedman ANOVA. Differences at the $p \leq 0.05$ level were considered to be statistically significant. For Formulation A, compared to ReNu® Wetting Drops, there were no statistically significant differences in comfort, lens movement/centration or anterior ocular physiology. A statistically significant increase in apparent lens Rx power was found for the test and control solution eyes after four hours. Mean difference in apparent lens Rx was less than –0.25D, which was considered clinically insignificant. After four hours, both test and control solution eyes showed a statistically lower sting/burn visual analog score (i.e. more sting/bum). In addition to the efficacy shown in Example 4 above, the Formulation A drop appeared to be safe and tolerable.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

What is claimed is:

1. A method of treating a silicone-hydrogel contact lens that is an extended-wear lens wom for an extended-wear period within the range of about 7 days to about 30 days to provide resistance to lipid deposition which method comprises treating the lens in the eye with eye drops of a sterile aqueous solution comprising:
    (a) 0.01 to 1.0 percent by weight of a cationic cellulosic polymer;
    (b) at least one tonicity agent which is present in an amount of 0.01 to 10.0% by weight; and
    (c) an effective amount of a buffering agent to maintain the pH from about 6 to about 8.

2. The method of claim 1, further comprising is 0.1 to 2.0 percent by weight of one or more surfactants.

3. The method of claim 1, wherein at least one surfactant is a polyoxyethylene-polyoxypropylene nonionic surfactant.

4. The method of claim 1, wherein the solution further comprises a wetting agent.

5. The method of claim 4, wherein the wetting agent is selected from the group consisting of glycerin, propylene glycol, mono or disaccharide, polyethylene glycol, ethoxylated glucose, and combinations thereof.

6. The method of claim 1, further comprising a polymeric nonionic demulcent.

7. The method of claim 1, wherein the solution further comprises an effective amount of a sequestering agent.

8. The method of claim 1, wherein the solution is applied by an an eye-drop dispenser and is stored in a container capable of holding between about 1 and about 30 ml of the solution.

9. The method of claim 1, wherein the solution is employed to clean the lens.

10. The method of claim 9, wherin the solution is employed to clean and/or prophylacticall clean lipid and/or protein deposits.

11. A method of treating a silicone-hydrogel contact lens that is an extended-wear lens worn for an extended-wear period within the range of about 7 days to about 30 days to provide resistance to lipid deposition which method comprises treating the lens in the eye with eye drops of a sterile aqueous solution comprising:
    (a) 0.01 to 1.0 percent by weight of a cationic cellulosic polymer;
    (b) 0.1 to 2.0 percent by weight of at least one surfactant, including a polyoxyethylene-polyoxypropylene nonionic surfactant;
    (c) an effective amount of a polymeric nonionic demulcent;
    (d) at least one tonicity agent which is present in an amount of 0.01 to 10.0% by weight; and
    (e) an effective amount of a buffering agent to maintain the pH from about 6 to about 8.

12. The method of claim 11, wherein the polymeric nonionic demulcent is povidone, polyvinyl alcohol, cellulose, and derivatives thereof.

13. The method of claim 11, wherein the solution further comprises a wetting agent selected from the group consisting of glycerin, propylene glycol, mono or disaccharide, polyethylene glycol, ethoxylated glucose, and comninations thereof.

* * * * *